United States Patent
Takeuchi et al.

(10) Patent No.: US 8,273,776 B2
(45) Date of Patent: Sep. 25, 2012

(54) BIPHENYL OXADIAZOLE DERIVATIVES AS SPHINGOSINE-1-PHOSPHATE RECEPTORS MODULATORS

(75) Inventors: Janet A. Takeuchi, Anaheim, CA (US); Ken Chow, Newport Coast, CA (US); Ling Li, Irvine, CA (US)

(73) Assignee: Allergan, Inc, Irvine, CA (US)

( * ) Notice: Subject to any disclaimer, the term of this patent is extended or adjusted under 35 U.S.C. 154(b) by 0 days.

(21) Appl. No.: 13/086,071

(22) Filed: Apr. 13, 2011

(65) Prior Publication Data

US 2011/0257232 A1 Oct. 20, 2011

Related U.S. Application Data

(60) Provisional application No. 61/324,945, filed on Apr. 16, 2010.

(51) Int. Cl.
*A61K 31/4245* (2006.01)
*C07D 271/06* (2006.01)

(52) U.S. Cl. ........ 514/364; 548/131

(58) Field of Classification Search ........ 514/364; 548/131

See application file for complete search history.

(56) References Cited

U.S. PATENT DOCUMENTS 7,799,812 B2 * 9/2010 Albert et al. ........ 514/364

OTHER PUBLICATIONS

Handbook of Pharmaceutical Salts, P.Heinrich Stahal& Camille G. Wermuth (Eds), Verlag Helvetica Chemica Acta—Zürich, 2002, 329-345.
Cross. "Rules for the Nomenclature of Organic Chemistry Section E: Stereochemistry" Pure Appli. Chem. (1976), 45, 11-13.

* cited by examiner

*Primary Examiner* — Yong Chu
(74) *Attorney, Agent, or Firm* — Doina G. Ene; John E. Wurst; Allergan, Inc.

(57) ABSTRACT

The present invention relates to novel biphenyl oxadiazole derivatives, processes for preparing them, pharmaceutical compositions containing them and their use as pharmaceuticals as modulators of sphingosine-1-phosphate receptors.

4 Claims, No Drawings

BIPHENYL OXADIAZOLE DERIVATIVES AS SPHINGOSINE-1-PHOSPHATE RECEPTORS MODULATORS

RELATED APPLICATIONS

This application is based on, and claims priority under 35 U.S.C. §120 to U.S. Provisional Application No. 61/324,945, filed on Apr. 19, 2010, and which is incorporated herein by reference.

FIELD OF THE INVENTION

The present invention relates to novel biphenyl oxadiazole derivatives, processes for preparing them, pharmaceutical compositions containing them and their use as pharmaceuticals as modulators of sphingosine-1-phosphate receptors. The invention relates specifically to the use of these compounds and their pharmaceutical compositions to treat disorders associated with sphingosine-1-phosphate (S1P) receptor modulation.

BACKGROUND OF THE INVENTION

Sphingosine-1 phosphate is stored in relatively high concentrations in human platelets, which lack the enzymes responsible for its catabolism, and it is released into the blood stream upon activation of physiological stimuli, such as growth factors, cytokines, and receptor agonists and antigens. It may also have a critical role in platelet aggregation and thrombosis and could aggravate cardiovascular diseases. On the other hand the relatively high concentration of the metabolite in high-density lipoproteins (HDL) may have beneficial implications for atherogenesis. For example, there are recent suggestions that sphingosine-1-phosphate, together with other lysolipids such as sphingosylphosphorylcholine and lysosulfatide, are responsible for the beneficial clinical effects of HDL by stimulating the production of the potent antiatherogenic signaling molecule nitric oxide by the vascular endothelium. In addition, like lysophosphatidic acid, it is a marker for certain types of cancer, and there is evidence that its role in cell division or proliferation may have an influence on the development of cancers. These are currently topics that are attracting great interest amongst medical researchers, and the potential for therapeutic intervention in sphingosine-1-phosphate metabolism is under active investigation.

SUMMARY OF THE INVENTION

We have now discovered a group of novel compounds which are potent and selective sphingosine-1-phosphate modulators. As such, the compounds described herein are useful in treating a wide variety of disorders associated with modulation of sphingosine-1-phosphate receptors. The term "modulator" as used herein, includes but is not limited to: receptor agonist, antagonist, inverse agonist, inverse antagonist, partial agonist, partial antagonist.

This invention describes compounds of Formula I, which have sphingosine-1-phosphate receptor biological activity. The compounds in accordance with the present invention are thus of use in medicine, for example in the treatment of humans with diseases and conditions that are alleviated by S1P modulation.

In one aspect, the invention provides a compound having Formula I or a pharmaceutically acceptable salt thereof or stereoisomeric forms thereof, or the geometrical isomers, enantiomers, diastereoisomers, tautomers, zwitterions and pharmaceutically acceptable salts thereof:

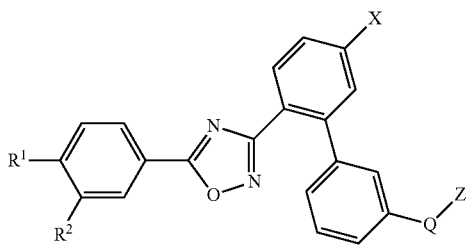

Formula I $R^1$ is $C_{1-10}$ alkyl, $C_{3-10}$ cycloalkyl, $-OC_{1-10}$ alkyl, hydroxyl, halogen, aryl, heterocycle;

$R^2$ is hydrogen, $C_{1-10}$ alkyl, $C_{3-10}$ cycloalkyl, $-OC_{1-10}$ alkyl, hydroxyl, halogen or nitrile;

X is hydrogen, halogen, Q or Z;

Q is $-(CH_2)_nN(C_{2-10})$alkylene-, $-O\ (C_{2-10})$alkylene- or $-S(C_{2-10})$alkylene-;

n is 0, 1, 2, 3, 4 or 5; and

Z is COOR, $SO_2NH_2$, $OPO_3H_2$ or $-P(O)(R)OH$; and

R is hydrogen, $C_{1-10}$ alkyl, $C_{3-10}$ cycloalkyl.

The term "alkyl", as used herein, refers to saturated, monovalent or divalent hydrocarbon moieties having linear or branched moieties or combinations thereof and containing 1-10 carbon atom. One methylene ($-CH_2-$) group, of the alkyl can be replaced by oxygen, sulfur, sulfoxide, nitrogen, carbonyl, carboxyl, sulfonyl, sulfate, or by a divalent $C_{3-6}$ cycloalkyl. Alkyl groups can be substituted by halogen, hydroxyl, cycloalkyl, amino, non-aromatic heterocycles, carboxylic acid, phosphonic acid groups, sulphonic acid groups, phosphoric acid.

The term "alkylene", as used herein, refers to saturated, divalent hydrocarbon moieties having linear or branched moieties or combinations thereof and containing 1-10 carbon atom. One methylene ($-CH_2-$) group, of the alkylene can be replaced by oxygen, sulfur, sulfoxide, nitrogen, carbonyl, carboxyl, sulfonyl, or by a divalent $C_{3-6}$ cycloalkyl. Alkylene groups can be substituted by halogen, hydroxyl, cycloalkyl, amino, heterocycles, carboxylic acid, phosphonic acid groups, sulphonic acid groups, phosphoric acid.

The term "cycloalkyl", as used herein, refers to a monovalent or divalent group of 3 to 10 carbon atoms derived from a saturated cyclic hydrocarbon. Cycloalkyl groups can be monocyclic or polycyclic. Cycloalkyl can be substituted by $C_{1-3}$ alkyl groups or halogens.

The term "halogen", as used herein, refers to an atom of chlorine, bromine, fluorine, iodine.

The term "heterocycle" as used herein, refers to a 3 to 10 membered ring, which can be aromatic or non-aromatic, saturated or non-saturated, containing at least one heteroatom selected from O or N or S or combinations of at least two thereof, interrupting the carbocyclic ring structure. The heterocyclic ring can be saturated or non-saturated. The heterocyclic ring can be interrupted by a C=O; the S heteroatom can be oxidized. Heterocycles can be monocyclic or polycyclic. Heterocyclic ring moieties can be substituted by hydroxyl, $C_{1-3}$ alkyl or halogens.

The term "hydroxyl" as used herein, represents a group of formula "—OH".

The term "carbonyl" as used herein, represents a group of formula "—C=O".

The term "carboxyl" as used herein, represents a group of formula "—C(O)O—".

The term "sulfonyl" as used herein, represents a group of formula "—SO$_2$".

The term "sulfate" as used herein, represents a group of formula "—O—S(O)$_2$—O—".

The term "carboxylic acid" as used herein, represents a group of formula "—C(O)ON".

The term "sulfoxide" as used herein, represents a group of formula "—S=O".

The term "phosphonic acid" as used herein, represents a group of formula "—P(O)(OH)$_2$".

The term "phosphoric acid" as used herein, represents a group of formula "—(O)P(O)(OH)$_2$".

The term "sulphonic acid" as used herein, represents a group of formula "—S(O)$_2$OH".

The formula "H", as used herein, represents a hydrogen atom.

The formula "O", as used herein, represents an oxygen atom.

The formula "N", as used herein, represents a nitrogen atom.

The formula "S", as used herein, represents a sulfur atom.

Some specific compounds of the present invention include:
(3-{2'-[5-(3-Cyano-4-isopropoxy-phenyl)-[1,2,4]oxadiazol-3-yl]-biphenyl-3-yloxy}-propylamino)-acetic acid;
(3-{2'-[5-(3'-Fluoro-2-trifluoromethyl-biphenyl-4-yl)-[1,2,4]oxadiazol-3-yl]-biphenyl-3-yloxy}-propylamino)acetic acid;
5-{3-[3'-(3-Hydroxy-propoxy)-biphenyl-2-yl]-[1,2,4]oxadiazol-5-yl}-2-isopropoxy-benzonitrile.

Some compounds of Formula I and some of their intermediates have at least one stereogenic center in their structure. This stereogenic center may be present in an R or S configuration, said R and S notation is used in correspondence with the rules described in Pure Appli. Chem. (1976), 45, 11-13.

The term "pharmaceutically acceptable salts" refers to salts or complexes that retain the desired biological activity of the above identified compounds and exhibit minimal or no undesired toxicological effects. The "pharmaceutically acceptable salts" according to the invention include therapeutically active, non-toxic base or acid salt forms, which the compounds of Formula I are able to form.

The acid addition salt form of a compound of Formula I that occurs in its free form as a base can be obtained by treating the free base with an appropriate acid such as an inorganic acid, such as for example hydrochloric acid, hydrobromic acid, sulfuric acid, phosphoric acid, nitric acid and the like; or an organic acid such as for example, acetic acid, hydroxyacetic acid, propanoic acid, lactic acid, pyruvic acid, malonic acid, fumaric acid, maleic acid, oxalic acid, tartaric acid, succinic acid, malic acid, ascorbic acid, benzoic acid, tannic acid, pamoic acid, citric acid, methylsulfonic acid, ethanesulfonic acid, benzenesulfonic acid, formic and the like (Handbook of Pharmaceutical Salts, P. Heinrich Stahal & Camille G. Wermuth (Eds), Verlag Helvetica Chemica Acta-Zürich, 2002, 329-345).

Compounds of Formula I and their salts can be in the form of a solvate, which is included within the scope of the present invention. Such solvates include for example hydrates, alcoholates and the like.

With respect to the present invention reference to a compound or compounds, is intended to encompass that compound in each of its possible isomeric forms and mixtures thereof unless the particular isomeric form is referred to specifically.

Compounds according to the present invention may exist in different polymorphic forms. Although not explicitly indicated in the above formula, such forms are intended to be included within the scope of the present invention.

The compounds of the invention are indicated for use in treating or preventing conditions in which there is likely to be a component involving the sphingosine-1-phosphate receptors.

In another embodiment, there are provided pharmaceutical compositions including at least one compound of the invention in a pharmaceutically acceptable carrier.

In a further embodiment of the invention, there are provided methods for treating disorders associated with modulation of sphingosine-1-phosphate receptors. Such methods can be performed, for example, by administering to a subject in need thereof a pharmaceutical composition containing a therapeutically effective amount of at least one compound of the invention.

These compounds are useful for the treatment of mammals, including humans, with a range of conditions and diseases that are alleviated by S1P modulation: not limited to the treatment of diabetic retinopathy, other retinal degenerative conditions, dry eye, angiogenesis and wounds.

Therapeutic utilities of S1P modulators are ocular diseases, such as but not limited to: wet and dry age-related macular degeneration, diabetic retinopathy, retinopathy of prematurity, retinal edema, geographic atrophy, glaucomatous optic neuropathy, chorioretinopathy, hypertensive retinopathy, ocular ischemic syndrome, prevention of inflammation-induced fibrosis in the back of the eye, various ocular inflammatory diseases including uveitis, scleritis, keratitis, and retinal vasculitis; or systemic vascular barrier related diseases such as but not limited to: various inflammatory diseases, including acute lung injury, its prevention, sepsis, tumor metastasis, atherosclerosis, pulmonary edemas, and ventilation-induced lung injury; or autoimmune diseases and immunosuppression such as but not limited to: rheumatoid arthritis, Crohn's disease, Graves' disease, inflammatory bowel disease, multiple sclerosis, Myasthenia gravis, Psoriasis, ulcerative colitis, antoimmune uveitis, renal ischemia/perfusion injury, contact hypersensitivity, atopic dermitatis, and organ transplantation; or allergies and other inflammatory diseases such as but not limited to: urticaria, bronchial asthma, and other airway inflammations including pulmonary emphysema and chronic obstructive pulmonary diseases; or cardiac protection such as but not limited to: ischemia reperfusion injury and atherosclerosis; or wound healing such as but not limited to: scar-free healing of wounds from cosmetic skin surgery, ocular surgery, GI surgery, general surgery, oral injuries, various mechanical, heat and burn injuries, prevention and treatment of photoaging and skin ageing, and prevention of radiation-induced injuries; or bone formation such as but not limited to: treatment of osteoporosis and various bone fractures including hip and ankles; or antinociceptive activity such as but not limited to: visceral pain, pain associated with diabetic neuropathy, rheumatoid arthritis, chronic knee and joint pain, tendonitis, osteoarthritis, neuropathic pains; or central nervous system neuronal activity in Alzheimer's disease, age-related neuronal injuries; or in organ transplant such as renal, corneal, cardiac or adipose tissue transplant.

In still another embodiment of the invention, there are provided methods for treating disorders associated with modulation of sphingosine-1-phosphate receptors. Such methods can be performed, for example, by administering to a subject in need thereof a therapeutically effective amount of at least one compound of the invention, or any combination thereof, or pharmaceutically acceptable salts, hydrates, solvates, crystal forms and individual isomers, enantiomers, and diastereomers thereof.

The present invention concerns the use of a compound of Formula I or a pharmaceutically acceptable salt thereof, for the manufacture of a medicament for the treatment of ocular disease, wet and dry age-related macular degeneration, diabetic retinopathy, retinopathy of prematurity, retinal edema, geographic atrophy, glaucomatous optic neuropathy, chorioretinopathy, hypertensive retinopathy, ocular ischemic syndrome, prevention of inflammation-induced fibrosis in the back of the eye, various ocular inflammatory diseases including uveitis, scleritis, keratitis, and retinal vasculitis; or systemic vascular barrier related diseases, various inflammatory diseases, including acute lung injury, its prevention, sepsis, tumor metastasis, atherosclerosis, pulmonary edemas, and ventilation-induced lung injury; or autoimmune diseases and immunosuppression, rheumatoid arthritis, Crohn's disease, Graves'disease, inflammatory bowel disease, multiple sclerosis, Myasthenia gravis, Psoriasis, ulcerative colitis, antoimmune uveitis, renal ischemia/perfusion injury, contact hypersensitivity, atopic dermititis, and organ transplantation; or allergies and other inflammatory diseases, urticaria, bronchial asthma, and other airway inflammations including pulmonary emphysema and chronic obstructive pulmonary diseases; or cardiac protection, ischemia reperfusion injury and atherosclerosis; or wound healing, scar-free healing of wounds from cosmetic skin surgery, ocular surgery, GI surgery, general surgery, oral injuries, various mechanical, heat and burn injuries, prevention and treatment of photoaging and skin ageing, and prevention of radiation-induced injuries; or bone formation, treatment of osteoporosis and various bone fractures including hip and ankles; or anti-nociceptive activity, visceral pain, pain associated with diabetic neuropathy, rheumatoid arthritis, chronic knee and joint pain, tendonitis, osteoarthritis, neuropathic pains; or central nervous system neuronal activity in Alzheimer's disease, age-related neuronal injuries; or in organ transplant such as renal, corneal, cardiac or adipose tissue transplant.

The actual amount of the compound to be administered in any given case will be determined by a physician taking into account the relevant circumstances, such as the severity of the condition, the age and weight of the patient, the patient's general physical condition, the cause of the condition, and the route of administration.

The patient will be administered the compound orally in any acceptable form, such as a tablet, liquid, capsule, powder and the like, or other routes may be desirable or necessary, particularly if the patient suffers from nausea. Such other routes may include, without exception, transdermal, parenteral, subcutaneous, intranasal, via an implant stent, intrathecal, intravitreal, topical to the eye, back to the eye, intramuscular, intravenous, and intrarectal modes of delivery. Additionally, the formulations may be designed to delay release of the active compound over a given period of time, or to carefully control the amount of drug released at a given time during the course of therapy.

In another embodiment of the invention, there are provided pharmaceutical compositions including at least one compound of the invention in a pharmaceutically acceptable carrier therefor. The phrase "pharmaceutically acceptable" means the carrier, diluent or excipient must be compatible with the other ingredients of the formulation and not deleterious to the recipient thereof.

Pharmaceutical compositions of the present invention can be used in the form of a solid, a solution, an emulsion, a dispersion, a micelle, a liposome, and the like, wherein the resulting composition contains one or more compounds of the present invention, as an active ingredient, in admixture with an organic or inorganic carrier or excipient suitable for enteral or parenteral applications. Invention compounds may be combined, for example, with the usual non-toxic, pharmaceutically acceptable carriers for tablets, pellets, capsules, suppositories, solutions, emulsions, suspensions, and any other form suitable for use. The carriers which can be used include glucose, lactose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening and coloring agents and perfumes may be used. Invention compounds are included in the pharmaceutical composition in an amount sufficient to produce the desired effect upon the process or disease condition.

Pharmaceutical compositions containing invention compounds may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of a sweetening agent such as sucrose, lactose, or saccharin, flavoring agents such as peppermint, oil of wintergreen or cherry, coloring agents and preserving agents in order to provide pharmaceutically elegant and palatable preparations. Tablets containing invention compounds in admixture with non-toxic pharmaceutically acceptable excipients may also be manufactured by known methods. The excipients used may be, for example, (1) inert diluents such as calcium carbonate, lactose, calcium phosphate or sodium phosphate; (2) granulating and disintegrating agents such as corn starch, potato starch or alginic acid; (3) binding agents such as gum tragacanth, corn starch, gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

In some cases, formulations for oral use may be in the form of hard gelatin capsules wherein the invention compounds are mixed with an inert solid diluent, for example, calcium carbonate, calcium phosphate or kaolin. They may also be in the form of soft gelatin capsules wherein the invention compounds are mixed with water or an oil medium, for example, peanut oil, liquid paraffin, or olive oil.

The pharmaceutical compositions may be in the form of a sterile injectable suspension. This suspension may be formulated according to known methods using suitable dispersing or wetting agents and suspending agents. The sterile injectable preparation may also be a sterile injectable solution or suspension in a non-toxic parenterally-acceptable diluent or solvent, for example, as a solution in 1,3-butanediol. Sterile, fixed oils are conventionally employed as a solvent or suspending medium. For this purpose any bland fixed oil may be employed including synthetic mono- or diglycerides, fatty acids (including oleic acid), naturally occurring vegetable oils like sesame oil, coconut oil, peanut oil, cottonseed oil, etc., or synthetic fatty vehicles like ethyl oleate or the like. Buffers, preservatives, antioxidants, and the like can be incorporated as required.

Invention compounds may also be administered in the form of suppositories for rectal administration of the drug. These compositions may be prepared by mixing the invention compounds with a suitable non-irritating excipient, such as cocoa butter, synthetic glyceride esters of polyethylene glycols, which are solid at ordinary temperatures, but liquify and/or dissolve in the rectal cavity to release the drug.

Since individual subjects may present a wide variation in severity of symptoms and each drug has its unique therapeutic characteristics, the precise mode of administration and dosage employed for each subject is left to the discretion of the practitioner.

The compounds and pharmaceutical compositions described herein are useful as medicaments in mammals, including humans, for treatment of diseases and or alleviations of conditions which are responsive to treatment by agonists or functional antagonists of sphingosine-1-phosphate receptors. Thus, in further embodiments of the invention, there are provided methods for treating a disorder associated with modulation of sphingosine-1-phosphate receptors. Such methods can be performed, for example, by administering to a subject in need thereof a pharmaceutical composition containing a therapeutically effective amount of at least one invention compound. As used herein, the term "therapeutically effective amount" means the amount of the pharmaceutical composition that will elicit the biological or medical response of a subject in need thereof that is being sought by the researcher, veterinarian, medical doctor or other clinician. In some embodiments, the subject in need thereof is a mammal. In some embodiments, the mammal is human.

The present invention concerns also processes for preparing the compounds of Formula I. The compounds of Formula I according to the invention can be prepared analogously to conventional methods as understood by the person skilled in the art of synthetic organic chemistry.

The synthetic scheme set forth below, illustrates how biphenyl oxadiazole derivatives according to the invention can be made. Those skilled in the art will be able to routinely modify and/or adapt the following scheme to synthesize any compounds of the invention covered by Formula I. The oxadiazole formation takes place under microwave induction followed by subsequent oxidation and reductive amination.

General scheme

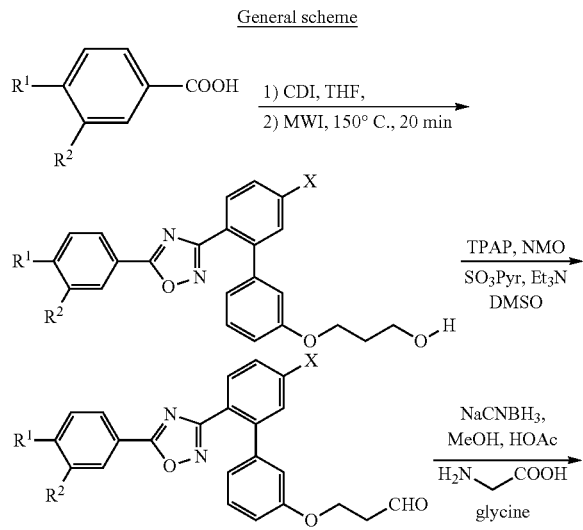

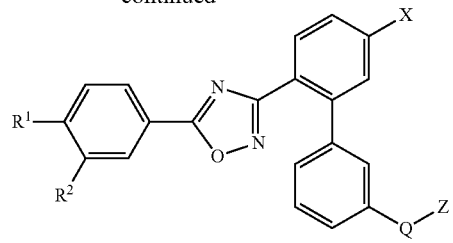

Formula I

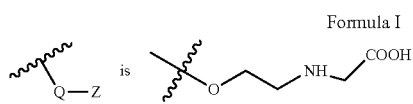

CDI N,N'-Carbonyldiimidazole
MWI microwave
TPAP Tetrapropylammonium Perruthenate
NMO N-methylmorpholine-N-oxide
$Et_3N$ triethylamine
DMSO dimethylsulfoxide
$NaCNBH_3$ sodiumcyanoborohydride
MeOH methanol
HOAc acetic acid

DETAILED DESCRIPTION OF THE INVENTION

It is to be understood that both the foregoing general description and the following detailed description are exemplary and explanatory only and are not restrictive of the invention claimed. As used herein, the use of the singular includes the plural unless specifically stated otherwise.

It will be readily apparent to those skilled in the art that some of the compounds of the invention may contain one or more asymmetric centers, such that the compounds may exist in enantiomeric as well as in diastereomeric forms. Unless it is specifically noted otherwise, the scope of the present invention includes all enantiomers, diastereomers and racemic mixtures. Some of the compounds of the invention may form salts with pharmaceutically acceptable acids or bases, and such pharmaceutically acceptable salts of the compounds described herein are also within the scope of the invention.

The present invention includes all pharmaceutically acceptable isotopically enriched compounds. Any compound of the invention may contain one or more isotopic atoms enriched or different than the natural ratio such as deuterium $^2H$ (or D) in place of protium $^1H$ (or H) or use of $^{13}C$ enriched material in place of $^{12}C$ and the like. Similar substitutions can be employed for N, O and S. The use of isotopes may assist in analytical as well as therapeutic aspects of the invention. For example, use of deuterium may increase the in vivo half-life by altering the metabolism (rate) of the compounds of the invention. These compounds can be prepared in accord with the preparations described by use of isotopically enriched reagents.

The following examples are for illustrative purposes only and are not intended, nor should they be construed as limiting the invention in any manner. Those skilled in the art will appreciate that variations and modifications of the following examples can be made without exceeding the spirit or scope of the invention.

As will be evident to those skilled in the art, individual isomeric forms can be obtained by separation of mixtures thereof in conventional manner. For example, in the case of diasteroisomeric isomers, chromatographic separation may be employed.

Compound names were generated with ACD version 8; and Intermediates and reagent names used in the examples were generated with software such as Chem Bio Draw Ultra version 12.0 or Auto Nom 2000 from MDL ISIS Draw 2.5 SP1.

In general, characterization of the compounds is performed according to the following methods:

NMR spectra are recorded on 300 and/or 600 MHz Varian and acquired at room temperature. Chemical shifts are given in ppm referenced either to internal TMS or to the solvent signal.

All the reagents, solvents, catalysts for which the synthesis is not described are purchased from chemical vendors such as Sigma Aldrich, Fluka, Bio-Blocks, Combi-blocks, TCI, VWR, Lancaster, Oakwood, Trans World Chemical, Alfa, Fisher, Maybridge, Frontier, Matrix, Ukrorgsynth, Toronto, Ryan Scientific, SiliCycle, Anaspec, Syn Chem, Chem-Impex, MIC-scientific, Ltd; however some known intermediates, were prepared according to published procedures.

Usually the compounds of the invention were purified by column chromatography (Auto-column) on an Teledyne-ISCO CombiFlash with a silica column, unless noted otherwise.

The following abbreviations are used in the examples:
R.T. room temperature
$MgSO_4$ magnesium sulfate
DMSO-$d_6$ deuterated dimethyl sulfoxide
MPLC medium pressure liquid chromatography
THF tetrahydrofuran The following synthetic schemes illustrate how compounds according to the invention can be made. Those skilled in the art will be routinely able to modify and/or adapt the following schemes to synthesize any compound of the invention covered by Formula I.

Some compounds of this invention can generally be prepared in one step from commercially available literature starting materials.

EXAMPLE 1

INTERMEDIATE 1

3'-fluoro-2-(trifluoromethyl)biphenyl-4-carboxylic acid

To a solution of [1,1'-Biphenyl]-4-carbonitrile, 3'-fluoro-2-(trifluoromethyl)-[CAS 1214368-40-7] (2.28 g, 8.6 mmol) in ethanol (75 mL) was added water (7.5 mL) and potassium hydroxide (481 mg, 8.6 mmol). After heating to reflux for over 24 h, the reaction mixture was cooled to RT, diluted with water and acidified to pH 2 with 10% HCl solution. The aqueous solution was extracted with ethyl acetate. The combined organic layers were washed with water and brine, dried ($MgSO_4$), filtered and concentrated under reduced pressure to afford 2.11 g of Intermediate 1 as a colorless solid. $^1$H NMR (600 MHz, chloroform-d) δ 8.52 (d, J=1.76 Hz, 1H), 8.32 (dd, J=1.47, 7.92 Hz, 1H), 7.48 (d, J=7.92 Hz, 1H), 7.41 (td, J=5.87, 7.92 Hz, 1H), 7.12-7.16 (m, 2H), 7.08 (dt, J=1.90, 9.24 Hz, 1H).

EXAMPLE 2

INTERMEDIATE 2

3'-(3-hydroxypropoxy)biphenyl-2-carbonitrile

To a solution of [1,1'-Biphenyl]-2-carbonitrile, 3'-hydroxy [CAS 154848-41-6] (2.4 g, 12 mmol) in isopropanol (115 mL) was added sodium hydroxide (2N, 42 mL) and 3-bromo-1-propanol (2.1 mL, 24 mmol). After stirring for 29 h at 70° C., the reaction mixture was cooled to RT and concentrated under reduced pressure, diluted with water and extracted with ethyl acetate. The combined organic layers were washed with water and brine, dried ($MgSO_4$), filtered and concentrated under reduced pressure. Purification of the residue by MPLC (5% ethyl acetate in hexanes) gave 2.9 g of Intermediate 2. $^1$H NMR (300 MHz, chloroform-d) δ 7.76 (dd, J=0.88, 7.62 Hz, 1H), 7.64 (td, J=1.17, 7.90 Hz, 1H), 7.52 (dd, J=0.59, 7.33 Hz, 1H), 7.37-7.47 (m, 2H), 7.10-7.15 (m, 2H), 7.00 (dd, J=2.34, 8.21 Hz, 1H), 4.18-4.26 (m, 2H), 3.88 (t, J=6.01 Hz, 2H), 2.03-2.12 (m, 2H), 1.82 (br. s., 1H).

EXAMPLE 3

INTERMEDIATE 3

N'-hydroxy-3'-(3-hydroxypropoxy)biphenyl-2-carboximidamide

To a solution of 3'-(3-hydroxypropoxy)biphenyl-2-carbonitrile (1.79 g, 7.07 mmol) in isopropanol (8 mL) was added hydroxylamine hydrochloride (1.3 mL). After heating to 80° C. with stirring for 40 h, the reaction mixture was cooled to RT and concentrated under reduced pressure. Purification of the residue by flash chromatography (50-100% ethyl acetate in hexanes) gave Intermediate 3. $^1$H NMR (300 MHz, DMSO-$d_6$) δ 9.19 (s, 1H, OH), 7.33-7.47 (m, 4H), 7.24 (t, J=7.77 Hz, 1H), 6.94-7.01 (m, 2H), 6.84 (dd, J=1.61, 8.35 Hz, 1H), 5.56 (s, 2H, NH2), 4.51 (t, J=4.84 Hz, 1H), 4.02 (t, J=6.30 Hz, 2H), 3.51-3.58 (m, 2H), 1.81-1.90 (m, 2H).

EXAMPLE 4

INTERMEDIATE 4

3-[(2'-{5-[3'-fluoro-2-(trifluoromethyl)biphenyl-4-yl]-1,2,4-oxadiazol-3-yl}biphenyl-3-yl)oxy]propan-1-ol To a solution of Intermediate 1 (543 mg, 1.8 mmol) in THF (8 mL) at RT was added 1,1'-carbonyldiimidazole (293 mg, 1.8 mmol). After stirring the reaction mixture for 30 min, a solution of Intermediate 3 (515 mg, 1.8 mmol) in THF (8 mL) was added. After stirring at 50° C. for 2 h, the reaction mixture was cooled, diluted with water and extracted with ethyl acetate. The combined organic layers were washed with water and brine, dried ($MgSO_4$), filtered and concentrated under reduced pressure. Purification of the residue by MPLC (60% ethyl acetate in hexanes) gave 700 mg of Intermediate 4. $^1$H NMR (300 MHz, chloroform-d) δ 8.44 (s, 1H), 8.22 (d, J=7.91 Hz, 1H), 7.94 (d, J=7.33 Hz, 1H), 7.46-7.61 (m, 4H), 7.36-7.44 (m, 1H), 7.22 (d, J=7.62 Hz, 1H), 7.03-7.17 (m, 3H), 6.86-6.93 (m, 3H), 4.10 (t, J=5.86 Hz, 2H), 3.81 (t, J=5.86 Hz, 2H), 2.30 (br. s., 1H), 2.00 (quin, J=5.90 Hz, 2H).

EXAMPLE 5

Compound 1

5-{3-[3'-(3-Hydroxy-propoxy)-biphenyl-2-yl]-[1,2,4]oxadiazol-5-yl}-2-isopropoxy-benzonitrile Compound 1 was synthesized according to the method described in Example 4 from 3-cyano-4-isopropoxybenzoic acid [CAS 258273-31-3] and Intermediate 3. $^1$H NMR (600

MHz, chloroform-d) δ 8.23 (dd, J=2.20, 4.26 Hz, 1H), 8.13-8.16 (m, 1H), 7.87-7.89 (m, 1H), 7.54-7.58 (m, 1H), 7.45-7.50 (m, 2H), 7.19-7.23 (m, 1H), 7.05 (dd, J=2.20, 8.95 Hz, 1H), 6.89-6.90 (m, 1H), 6.83-6.88 (m, 2H), 4.75 (dtd, J=3.37, 6.03, 12.14 Hz, 1H), 4.07-4.14 (m, 2H), 3.78-3.82 (m, 2H), 1.99 (sxt, J=5.99 Hz, 2H), 1.44 (d, J=6.16 Hz, 3H), 1.44 (d, J=5.87 Hz, 3H).

EXAMPLE 6

INTERMEDIATE 5

3-[(2'-5-[3'-fluoro-2-(trifluoromethyl)biphenyl-4-yl]-1,2,4-oxadiazol-3-ylbiphenyl-3-yl)oxy]propanal To a solution of Intermediate 4 (700 mg, 1.3 mmol) in dichloromethane (12 mL) and acetonitrile (1.6 mL) were added 4 Å molecular sieves, powdered, 4-methylmorpholine N-oxide (383 mg, 3.2 mmol), tetrapropylammonium perruthenate (10 mg). After stirring for 2 h, the reaction mixture was applied directly to a short silica gel plug (25% ethyl acetate in hexanes) to afford Intermediate 5 as a colorless oil. The product was used directly in the next step without further purification. $^1$H NMR (300 MHz, chloroform-d) δ 9.82 (s, 1H), 8.44 (s, 1H), 8.21 (t, J=7.90 Hz, 1H), 7.94 (t, J=6.15 Hz, 1H), 7.34-7.62 (m, 5H), 7.03-7.28 (m, 4H), 6.79-6.93 (m, 3H), 4.29 (t, J=6.15 Hz, 2H), 2.86 (td, J=1.32, 6.08 Hz, 2H).

EXAMPLE 7

INTERMEDIATE 6

2-isopropoxy-5-3-[3'-(4-oxobutoxy)biphenyl-2-yl]-1,2,4-oxadiazol-5-ylbenzonitrile To a solution of Compound 1 (305 mg, 0.67 mmol) in DMSO (2 mL) was added triethyl amine (0.28 mL, 2.01 mmol) with stirring. The solution was cooled to 0° C. and a solution of sulfur trioxide pyridine complex (320 mg, 2.01 mmol) in DMSO (2 mL) was added and stirred at RT for 1 h. The reaction mixture was poured onto ice water and extracted with ethyl acetate. The combined organic layers were washed with 10% acetic acid, water, 5% sodium bicarbonate, brine, dried (MgSO$_4$), filtered and concentrated under reduced pressure. Purification of the residue by flash chromatography (5% ethyl acetate in hexanes) gave 218 mg of Intermediate 6 as a colorless oil. $^1$H NMR (300 MHz, chloroform-d) δ 9.83 (s, 1H), 8.23 (dd, J=2.05, 3.22 Hz, 1H), 8.14 (ddd, J=2.34, 4.54, 8.94 Hz, 1H), 7.88 (t, J=7.33 Hz, 1H), 7.40-7.60 (m, 3H), 7.12-7.27 (m, 1H), 7.05 (dd, J=5.86, 8.79 Hz, 1H), 6.72-6.90 (m, 3H), 4.70-4.80 (m, 1H), 4.28 (t, J=6.15 Hz, 2H), 2.86 (td, J=1.32, 6.08 Hz, 2H), 1.44 (d, J=5.86 Hz, 3H), 1.44 (d, J=6.15 Hz, 3H).

EXAMPLE 8

Compound 2

(3-{2'-[5-(3'-Fluoro-2-trifluoromethyl-biphenyl-4-yl)-[1,2,4]oxadiazol-3-yl]-biphenyl-3-yloxy}-propylamino)acetic acid To a solution of Intermediate 5 (170 mg, 0.32 mmol) in methanol (8 mL) and dichloromethane (2 mL) was added glycine (36 mg, 0.48 mmol). After stirring the reaction mixture for 1 h, sodium cyanoborohydride (20 mg, 0.32 mmol) was added and stirred for another 2 h at RT. The reaction mixture was quenched with water and concentrated under reduced pressure. The residue was purified by reverse phase MPLC (90% to 10% water in acetonitrile) to yield 17 mg of Compound 2. $^1$H NMR (300 MHz, methanol-d$_4$) δ 8.39 (s, 1H), 8.30 (d, J=7.62 Hz, 1H), 7.90 (d, J=7.33 Hz, 1H), 7.44-7.68 (m, 5H), 7.10-7.26 (m, 4H), 6.90-6.95 (m, 2H), 6.83 (d, J=7.33 Hz, 1H), 4.07 (t, J=6.01 Hz, 2H), 3.37 (s, 2H), 3.04 (t, J=7.33 Hz, 2H), 2.03-2.13 (m, 2H).

EXAMPLE 9

Compound 3

(3-{2'-[5-(3-Cyano-4-isopropoxy-phenyl)-[1,2,4]oxadiazol-3-yl]-biphenyl-3-yloxy}-propylamino)-acetic acid Compound 3 was synthesized according the procedure from Example 8 from Intermediate 6. $^1$H NMR (300 MHz, methanol-d$_4$) δ 8.20-8.25 (m, 2H), 7.84 (d, J=7.62 Hz, 1H), 7.63 (t, J=7.60 Hz, 1H), 7.53 (t, J=7.30 Hz, 1H), 7.51 (t, J=7.77 Hz, 1H), 7.37 (d, J=9.38 Hz, 1H), 7.22 (t, J=7.77 Hz, 1H), 6.90-6.95 (m, 2H), 6.81 (d, J=7.62 Hz, 1H), 4.58 (br. s., 1H), 4.09 (t, J=5.42 Hz, 1H), 3.48-3.56 (m, 2H), 3.34-3.40 (m, 2H), 3.19 (t, J=7.03 Hz, 2H), 2.10-2.22 (m, 2H), 1.43 (d, J=6.15 Hz, 6H).

Biological Data

Compounds were synthesized and tested for S1P1 activity using the GTP γ$^{35}$S binding assay. These compounds may be assessed for their ability to activate or block activation of the human S1P1 receptor in cells stably expressing the S1P1 receptor.

GTP γ$^{35}$S binding was measured in the medium containing (mM) HEPES 25, pH 7.4, MgCl$_2$ 10, NaCl 100, dithitothreitol 0.5, digitonin 0.003%, 0.2 nM GTP γ$^{35}$S, and 5 μg membrane protein in a volume of 150 μl. Test compounds were included in the concentration range from 0.08 to 5,000 nM unless indicated otherwise. Membranes were incubated with 100 μM 5'-adenylylimmidodiphosphate for 30 min, and subsequently with 10 μM GDP for 10 min on ice. Drug solutions and membrane were mixed, and then reactions were initiated by adding GTP γ$^{35}$S and continued for 30 min at 25° C. Reaction mixtures were filtered over Whatman GF/B filters under vacuum, and washed three times with 3 mL of ice-cold buffer (HEPES 25, pH7.4, MgCl$_2$ 10 and NaCl 100). Filters were dried and mixed with scintillant, and counted for $^{35}$S activity using a β-counter. Agonist-induced GTP γ$^{35}$S binding was obtained by subtracting that in the absence of agonist. Binding data were analyzed using a non-linear regression method. In case of antagonist assay, the reaction mixture contained 10 nM S1P in the presence of test antagonist at concentrations ranging from 0.08 to 5000 nM.

Table 1 shows activity potency: S1 P1 receptor from GTP γ$^{35}$S: nM, (EC$_{50}$).

TABLE 1

| IUPAC name | S1P1 GTPγ$^{35}$S EC50 (nM) | % S1P1 STIMULATION @ 5 μM (%) |
|---|---|---|
| 5-{3-[3'-(3-Hydroxy-propoxy)-biphenyl-2-yl]-[1,2,4]oxadiazol-5-yl}-2-isopropoxy-benzonitrile | 1416 | 76 |
| (3-{2'-[5-(3-Cyano-4-isopropoxy-phenyl)-[1,2,4]oxadiazol-3-yl]- | 82 | 85 |

TABLE 1-continued

| IUPAC name | S1P1 GTPγ$^{35}$S EC50 (nM) | % S1P1 STIMULATION @ 5 μM (%) |
|---|---|---|
| biphenyl-3-yloxy}-propylamino)-acetic acid | | |
| (3-{2'-[5-(3'-Fluoro-2-trifluoromethyl-biphenyl-4-yl)-[1,2,4]oxadiazol-3-yl]-biphenyl-3-yloxy}-propylamino)-acetic acid | 552 | 96 |

What is claimed is:

1. A compound represented by Formula I, its individual enantiomers, individual diastereoisomers, individual tautomers or a pharmaceutically acceptable salt thereof,

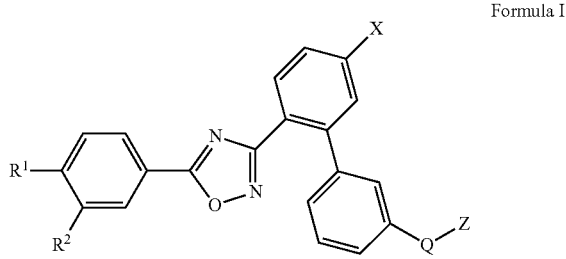

Formula I

R$^1$ is C$_{1-10}$ alkyl, C$_{3-10}$ cycloalkyl, —OC$_{1-10}$ alkyl, —OH, halogen, aryl, heterocycle;

R$^2$ is H, C$_{1-10}$ alkyl, C$_{3-10}$ cycloalkyl, —OC$_{1-10}$ alkyl, —OH, halogen or nitrile;

X is H, halogen, or Z;

Q is —(CH$_2$)$_n$N(C$_{2-10}$)alkylene-, —O(C$_{2-10}$)alkylene- or —S(C$_{2-10}$)alkylene-;

n is 0, 1, 2, 3, 4 or 5; and

Z is COOR, SO$_2$NH$_2$, OPO$_3$H$_2$ or —P(O)(R)OH; and

R is H, C$_{1-10}$ alkyl, C$_{3-10}$ cycloalkyl.

2. A compound according to claim 1 selected from:
(3-{2'-[5-(3-Cyano-4-isopropoxy-phenyl)-[1,2,4]oxadiazol-3-yl]-biphenyl-3-yloxy}-propylamino)-acetic acid;
(3-{2'-[5-(3'-Fluoro-2-trifluoromethyl-biphenyl-4-yl)-[1,2,4]oxadiazol-3-yl]-biphenyl-3-yloxy}-propylamino)-acetic acid; and
5-{3-[3'-(3-Hydroxy-propoxy)-biphenyl-2-yl]-[1,2,4]oxadiazol-5-yl}-2-isopropoxy-benzonitrile.

3. A pharmaceutical composition comprising as active ingredient a therapeutically effective amount of a compound according to claim 1 and a pharmaceutically acceptable adjuvant, diluents or carrier.

4. A pharmaceutical composition according to claim 3 wherein the compound is selected from:
(3-{2'-[5-(3-Cyano-4-isopropoxy-phenyl)-[1,2,4]oxadiazol-3-yl]-biphenyl-3-yloxy}-propylamino)-acetic acid;
(3-{2'-[5-(3'-Fluoro-2-trifluoromethyl-biphenyl-4-yl)-[1,2,4]oxadiazol-3-yl]-biphenyl-3-yloxy}-propylamino)-acetic acid; and
5-{3-[3'-(3-Hydroxy-propoxy)-biphenyl-2-yl]-[1,2,4]oxadiazol-5-yl}-2-isopropoxy-benzonitrile.

* * * * *